(12) United States Patent
Glasky et al.

(10) Patent No.: US 6,849,735 B1
(45) Date of Patent: Feb. 1, 2005

(54) METHODS OF SYNTHESIS FOR 9-SUBSTITUTED HYPOXANTHINE DERIVATIVES

(75) Inventors: Alvin J. Glasky, Tustin, CA (US); Heinrich Bollinger, Beringen (CH); Hans Rudolf Müller, Schaffhausen (CH)

(73) Assignee: Merck Eprova AG, Schaffhausen (CH)

( * ) Notice: Subject to any disclaimer, the term of this patent is extended or adjusted under 35 U.S.C. 154(b) by 0 days.

(21) Appl. No.: 09/602,048

(22) Filed: Jun. 23, 2000

(51) Int. Cl.$^7$ .................... C07D 473/30; C07D 233/90
(52) U.S. Cl. .................... 544/265; 548/326.5
(58) Field of Search .......................... 544/265

(56) References Cited

U.S. PATENT DOCUMENTS

| | | |
|---|---|---|
| 3,300,380 A | 1/1967 | Gray et al. |
| 3,321,369 A | 5/1967 | Glasky et al. |
| 3,438,968 A | 4/1969 | Glasky et al. |
| 3,666,856 A | 5/1972 | Elion et al. |
| 4,035,486 A | 7/1977 | Laborit |
| 4,138,562 A | 2/1979 | Vince |
| 4,221,794 A | 9/1980 | Simon et al. |
| 4,221,909 A | 9/1980 | Simon et al. |
| 4,221,910 A | 9/1980 | Giner-Sorolla |
| 4,315,920 A | 2/1982 | Schaeffer et al. |
| 4,340,726 A | 7/1982 | Simon et al. |
| 4,347,360 A | 8/1982 | Ogilvie |
| 4,451,478 A | 5/1984 | Simon et al. |
| 4,643,992 A | 2/1987 | Goodman et al. |
| 4,914,028 A * | 4/1990 | Hertel .................... 435/88 |
| 4,952,693 A | 8/1990 | Sircar et al. |
| 4,983,494 A * | 1/1991 | Kitaguchi .................... 430/203 |
| 5,023,294 A | 6/1991 | Goto et al. |
| 5,091,432 A | 2/1992 | Glasky |

(List continued on next page.)

FOREIGN PATENT DOCUMENTS

| | | |
|---|---|---|
| EP | 0924195 | 6/1999 |
| WO | WP 99/56550 | 11/1999 |
| WO | WO 99/57119 | 11/1999 |
| WO | WO 99/57120 | 11/1999 |

OTHER PUBLICATIONS

N. W. Tietz, ed., "Textbook of Clinical Chemistry" (W.B. Saunders Co., Philadelphia, 1986), pp. 882–886.

(List continued on next page.)

*Primary Examiner*—Mark L Berch
(74) *Attorney, Agent, or Firm*—Louis C. Cullman

(57) ABSTRACT

An improved method of synthesis of a 9-substituted hypoxanthine derivative comprises the steps of: (1) reacting aminocyanacetamide with triethyl orthoformate to form an imidoester derivative of aminocyanacetamide; (2) forming a compound having a reactive amino group on a hydrocarbyl moiety, the hydrocarbyl moiety being linked through an amide group to a physiologically active moiety or an esterified derivative of a physiologically active moiety including therein an esterified benzoyl group; (3) reacting the imidoester with the compound having the reactive amino group on the hydrocarbyl moiety to form a derivative of aminoimidazole-4-carboxamide substituted at the 1-position with a hydrocarbyl moiety linked through an amide group to a physiologically active moiety including therein an optionally esterified benzoyl group; (4) forming the six-membered heterocyclic ring of the purine moiety of the hypoxanthine by reacting the derivative of 5-aminoimidazole-4-carboxamide formed in step (3) with triethyl orthoformate to form a 9-substituted hypoxanthine compound substituted at the 9-position with a hydrocarbyl moiety linked through an amide group to a physiologically active moiety including therein an optionally esterified benzoyl group; and (5) hydrolyzing the ester of the optionally esterified benzoyl group if present.

1 Claim, 4 Drawing Sheets

U.S. PATENT DOCUMENTS

| | | | |
|---|---|---|---|
| 5,093,318 A | | 3/1992 | Goodman et al. |
| 5,187,162 A | | 2/1993 | Marangos et al. |
| 5,192,749 A | * | 3/1993 | O-Yang .................... 514/45 |
| 5,237,051 A | | 8/1993 | Garbers et al. |
| 5,256,677 A | | 10/1993 | Sham et al. |
| 5,376,642 A | | 12/1994 | Yarchoan et al. |
| 5,447,936 A | | 9/1995 | Glasky |
| 5,565,437 A | | 10/1996 | Marquez et al. |
| 5,595,901 A | | 1/1997 | Rocancourt et al. |
| 5,795,756 A | | 8/1998 | Johnson et al. |
| 5,801,159 A | | 9/1998 | Miller et al. |
| 5,801,184 A | | 9/1998 | Glasky |
| 5,861,532 A | * | 1/1999 | Brown .................... 564/142 |
| 5,948,771 A | | 9/1999 | Danziger |
| 6,027,936 A | | 2/2000 | Glasky |

OTHER PUBLICATIONS

G.A. Lyles & B.A. Callingham, "The Effects of Thyroid Hormones on Monoamine Oxidase in the Rat Heart," *J. Pharm. Pharmacol.* 26: 921–930 (1974).

S.K. Gupta & R.K. Mishra, "Desensitization of $D_1$ Dopamine Receptors Down–Regulates the $G_s\alpha$ Subunit of G Protein in SK–N–MC Neuroblastoma Cells," *J. Mol. Neurosci.* 4: 117–123 (1993).

S.K. Gupta & R.K. Mishra, "Up–Regulation of $D_1$ Dopamine Receptors in SK–N–MC Cells After Chronic Treatment with SCH 23390," *Neurosci. Res. Commun.* 15: 157–166 (1994).

P.W. Baures et al., "Design, Synthesis, X–Ray Analysis, and Dopamine Receptor–Modulating Activity of Mimics of the 'C5' Hydrogen–Bonded Conformation in the Peptidomimetic 2–Oxo–3–(R)–[(2(S)–Pyrrolidinylcarbonyl)amino]–1–Pyrrolidineacetamide," *J. Med. Chem.* 37: 3677–3683 (1994).

J.E. Savelli et al., "Modulation of N–Methyl–D–Aspartate (NMDA) Antagonist–Induced Darting Behaviour by the Peptidomimetic PAMTA," *Brain Res.* 682:41–49 (1995).

K.A. Jacobson, "Chemical Approaches to the Definition of Adenosine Receptors" in *Adenosine Receptors* (D.M.F. Cooper & C. Londos, eds., *Receptor Biochemistry and Methodology*, J.C. Venter, L.C. Harrison, eds., Alan R. Liss: New York, 1988), pp. 11:1–26.

S.H. Appel & J.L. McManaman, "Is a Breakdown of the Blood–Brain Barrier Cause or Effect?," *Neurobiol. Aging* 7:512–514 (1986).

S.M. MacDonald et al., "Immunological Parameters in the Aged and in Alzheimer's Disease," *Clin. Exp. Immunol.* 49:123–128 (1982).

A.E. Miller et al., "Immunological Studies in Senile Dementia of the Alzheimer Type: Evidence for Enhanced Suppressor Cell Activity," *Ann. Neurol.* 10:506–510 (1981).

K. Stefansson, "Neuroimmunology of Aging" in *Clinical Neurology of Aging* (M.L. Albert, ed., Oxford University Press, Oxford, (1984)), ch. 4, pp. 76–94.

L.R. Weitkamp et al., "Alzheimer Disease: Evidence for Susceptibility Loci on Chromosomes 6 and 14," *Am. J. Hum. Genet.* 35:443–53 (1983).

A. Yamakazi et al., Synthesis of Guanosine and Its Derivatives from 5–Amino–1–β–D–Ribofuranosyl–4–Imidazolecarboxamide I. Ring Closure with Benzoyl Isothiocyanate, *J. Org. Chem.* 32:1825–1828 (1967).

B. Alhede et al., "A Simple and Efficient Synthesis of 9–Substituted Guanines. Cyclodesulfurization of 1–Substituted 5[(Thiocarbamoyl)amino]imidazole–4–carboxamides under Aqueous Basic Conditions," *J. Org. Chem.* 56:2139–2143 (1991).

R.E. Callard & A.J.H. Gearing, "The Cytokine Facts Book" (Academic Press, London, 1994), pp. 99–100, 104–105, 191–200, 235–237.

P.J. Middlemiss et al., "AIT–082, a Unique Purine Derivative, Enhances Nerve Growth Factor Mediated Neurite Outgrowth from PC12 Cells," *Neurosci. Lett.* 199: 131–134 (1995).

K.L. Audus et al., "Brain Uptake of Drugs: the Influence of Chemical and Biological Factors," *Adv. Drug Res.* 23: 1–64 (1992).

W.A. Banks & A.J. Kastin, "Measurement of Transport of Cytokines Across the Blood–Brain Barrier," *Meth. Neurosci.* 16: 67–77 (1993).

A.L. Betz, "Identification of Hypoxanthine Transport and Xanthine Oxidase Activity in Brain Capillaries," *J. Neurochem.* 44: 574–579 (1985).

F.G. Blasberg et al., "Transport of α–Aminoisobutyric Acid Across Brain Capillary and Cellular Membranes," *J. Cereb. Blood Flow Metab.* 3: 8–32 (1983).

E.M. Cornford & W.H. Olendorf, "Independent Blood–Brain Barrier Transport Systems for Nucleic Acid Precursors," *Biochim. Biophys. Acta* 394: 211–219 (1975).

A.J. Glasky et al., "Effect of AIT–082, a Purine Analog, on Working Memory in Normal and Aged Mice," *Pharmacol. Biochem. Behav.* 47: 325–329 (1994).

A.J. Glasky et al., "Neurotrophins, Growth Factors and Mimetic Agents as Neuroprotectors in the Treatment of Alzheimer's Disease" in *Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20: 117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Mooradian, "Effect of Aging on the Blood–Brain Barrier," *Neurobiol. Aging* 9: 31–39 (1988).

W. Pan et al., "Permeability of the Blood–Brain Barrier to Neurotrophins," *Brain Res.* 788: 87–94 (1998).

W.M. Pardridge, "CNS Drug Design Based on Principles of Blood–Brain Barrier Transport," *J. Neurochem.* 70: 1781–1792 (1998).

J.F. Poduslo et al., "Macromolecular Permeability Across the Blood–Nerve and Blood–Brain Barriers," *Proc. Natl. Acad. Sci. USA* 91: 5705–5709 (1994).

J.F. Poduslo & G.L. Curran, "Permeability at the Blood–Brain Barrier and Blood–Nerve Barriers of the Neurotrophic Factors: NGF, CNTF, NT–3, BDNF," *Mol. Brain Res.* 36: 280–286 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–519 (1997).

I. Skoog et al., "A Population Study on Blood–Brain Barrier Function in 85–Year–Olds: Relation to Alzheimer's Disease and Vascular Dementia," *Neurology* 50: 966–971 (1998).

R. Spector, "Hypoxanthine Transport Through the Blood–Brain Barrier," *Neurochem. Res.* 12: 791–796 (1987).

R. Spector, "Hypoxanthine Transport and Metabolism in the Central Nervous System," *J. Neurochem.* 50: 969–978 (1988).

D. Triguero et al., "Capillary Depletion Method for Quantitation of Blood–Brain Barrier Transport of Circulating Peptides and Plasma Proteins," *J. Neurochem.* 54: 1882–1888 (1990).

W.A. Banks et al., "Measurement of Efflux Rates from Brain to Blood" in *Methods in Molecular Biology, Neuropeptide Protocols* (G.B. Irvine & C.H. Williams, eds., Humana Press, Totowa, NJ, 1997), pp. 353–360.

M.P. Rathbone et al., "Physiology and Pharmacology of Natural and Synthetic Nonadenine–Based Purines in the Nervous System," *Drug Develop. Res.* 45: 356–372 (1998).

M.P. Rathbone et al., AIT–082 as a Potential Neuroprotective and Regenerative Agent in Stroke and Central Nervous System Injury, *Exp. Opin. Invest. Drugs* 8: 1255–1262 (1999).

W.A. Banks et al., "Effects of Wheatgerm Agglutinin and Aging on the Regional Brain Uptake of HIV–1 gp120," *Life Sci.* 65: 81–89 (1999).

J.S. Bintner et al., "AIT–082, a Hypoxanthine Derivative, Prevents Much of the Decrease in Cerebellar Neuron ATP Following Glutamate Exposure," *Soc. Neurosci.* 25: 2131 (1999) (abstract).

R. Huang et al., "Enhancement of Neuronal Cell Excitability by AIT–082 in Rat Hippocampal Neurons and Its Effects on Second Messenger Systems," *Soc. Neurosci.* 24: 1941 (1998) (abstract).

O.Chu–LaGraff et al., "Effect of AIT–082 on Brain NGF mRNA Levels and Transport of AIT–082 Across the Blood–Brain Barrier," *Soc. Neurosci.* 24: 1941 (1998) (abstract).

F. Caciagli et al., "The Hypoxanthine Derivative AIT–082 Protects Against Neurotoxicity in Vitro and in Vivo," *Soc. Neurosci.* 24: 1941 (1998) (abstract).

B.H.J. Juurlink et al., "The Hypoxanthine Analogue AIT–082 Promotes Neurite Formation and Regeneration in Cultured Hippocampal Neurons," *Soc. Neurosci.* 24: 1941 (1998) (abstract).

E.M. Taylor et al., "$^{14}$C–AIT082 Crosses the Blood–Brain Barrier and Is Pumped Out of Brain by a Probenecid– and Verapamil–Sensitive Mechanism," *Soc. Neurosci.* 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," *Soc. Neurosci.* 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," *Soc. Neurosci.* 25: 1013 (1999) (abstract).

P.J. Middlemiss et al., "The Synthetic Purine AIT–082 Enhances Recovery After Acute Spinal Cord Crush Injury in Rats," *Soc. Neurosci.* 25: 1002 (1999) (abstract).

P. Di Iorio et al., "The Hypoxanthine Derivative AIT–082 Is Protective Against NMDA– or Kainic Acid–Induced Rat Hippocampal Neurotoxicity in Vivo," *Soc. Neurosci.* 25: 756 (1999) (abstract).

A.G. Gittis & J.R. Puzuasky, "AIT–082 Improves Memory Performance in a Non–Match–to–Sample Task in Rats," *Soc. Neurosci.* 25: 62 (1999) (abstract).

G. Shaw et al., "Purines, Pyrimidines, and Glyoxalines. Part XIII. Some New Unambiguous Syntheses of 5–Aminoglyoxalines and 5–Aminoglyoxaline–4–carboxamides, and a Synthesis of 5–Amino–1–β–D–ribofuranosylglyoxaline–4–carboxyamide," *J. Chem. Soc. 1959*: 1648– (1959).

P.R. Birkett et al., "Synthesis and Intramolecular Cyclisation of 5–Aminoimidazolealkanoates and Their Conversion to Purine Derivatives," *Synthesis* 1991:157–159 (1991).

G.M. Blackburn & M.J. Gait, eds., *Nucleic Acids in Chemistry and Biology* (2d ed., Oxford University Press, 1996), pp. 148–152.

* cited by examiner

HC(OEt)₃  
———————→  
Acetic acid

Hydrolysis  
KOH, HCl  
———————→

METHODS OF SYNTHESIS FOR 9-SUBSTITUTED HYPOXANTHINE DERIVATIVES

FIELD OF THE INVENTION

This invention is directed to improved synthetic methods for 9-substituted hypoxanthine compounds, particularly the 9-substituted hypoxanthine derivative N-4-carboxyphenyl-3-(6-oxohydropurin-9-yl) propanamide.

BACKGROUND OF THE INVENTION

The modification of pharmaceutical and biologically active compounds to alter or enhance their functional properties is known in the art. Typically, prior art efforts have been directed to the production of carrier-bound drugs in which carrier molecules having selective physical properties, such as enhanced water solubility, are chemically attached to biologically active compounds. For example, Jacobson and colleagues have developed what is referred to as the "functional congener" approach to the design of carrier-bound drugs (K. A. Jacobson, in Adenosine Receptors (D.M.F. Cooper & C. Londos, eds., Receptor Biochemistry and Methodology, J. C. Venter, L. C. Harrison, eds., Alan R. Liss: New York, 1988), pp. 11:1–26). This approach involved the modification of well defined drug molecules at non-sensitive positions in a manner that retained the drug's ability to bind at its specific receptor site. In order to produce a chemically functionalized drug congener, they modified the drug molecule through the introduction of a chemical functional group which could then covalently attached to a carrier molecule. This produced a bifunctional molecule in which one portion (the "pharmacophore") contributed its biological activity, and the second portion, or carrier, imparted its selective physical properties such as enhanced receptor attachment or water solubility. Using this approach, functional congener compounds were prepared utilizing catecholamines, adenosine receptor agonists and antagonists, and muscarinic agents.

However, recent developments in the understanding of biological mechanisms such as the binding of selective ligands to receptors and their related functions in such seemingly diverse physiological systems as the cardiovascular system, the central nervous system, and the immune system have stimulated efforts to discover alternative methods for designing biologically active compounds exhibiting properties which will selectively treat or regulate such seemingly diverse chemical systems without serious or disabling side effects. For example, adenosine receptors have been found in the cardiovascular system, in the central nervous system, and in the immune system. Accordingly, it was originally believed that the development of adenosine analogues would be effective at regulating or modifying the biological activities associated therewith. However, the ubiquitous distribution of adenosine receptors has resulted in the production of serious and disabling side effects in what were originally believed to be unrelated biological systems, thereby significantly reducing the therapeutic usefulness of adenosine analogues.

Similar interrelationships have also been discovered to exist in the mammalian immune system and in the mammalian nervous system. Over the past several decades numerous researchers have added considerable detail to the overall understanding of the mammalian immune system and its importance in maintaining overall physical health. In more recent years, similar detail has evolved in the study of the mammalian nervous system. As more and more information was developed in these seemingly independent fields of study, a number of close functional parallels began to appear between the two physiological systems. For example, both systems are concerned with the storage of information and use soluble chemicals to transmit signals between cells. Additionally, natural endogenous substances, such as hormones and transmitters, are active on the cells of both systems. Even more significantly, some common functions between the two systems are based upon similar chemical structures or markers on the surfaces of both nerve cells and immune cells. The recent discovery that the CD4 receptors targeted by the AIDS virus are present on both the T4 lymphocytes and on neurons is one of the more dramatic examples of the close relationship between the nervous system and the immune system.

Further crossing the classically imposed barriers between the fields of immunology and neurology, recent developments in the understanding of Alzheimer's disease have implicated an immunological component that may be present in this neurological disorder. It has been proposed that both the anatomical and biochemical specificity of the defects seen in Alzheimer's disease could be explained by an immunological attack on the brain blood vessels themselves with secondary involvement of neuronal, glial, or synaptic constituents contributing to the formation of senile plaques, or an immune-mediated compromise of vessels associated with an immune attack on specific neuronal, glial, or synaptic constituents (S. H. Appel, Neurobiol. Aging 7:512 (1986)).

Additionally, circumstantial evidence for an immunological component in neurological disorders is also provided by the altered suppressor cell function in aging populations, and more specifically in Alzheimer's disease (MacDonald et al., Clin. Exp. Immunol. 49:123–128 (1982); A. E. Miller, Ann. Neurol. 10:506–510 (1981); K. Stefansson in Clinical Neurology of Aging (M. L. Albert, ed., Oxford University Press, Oxford, (1984), pp. 7694) the implication of the existence of HLA regions of chromosome 6 and the GM locus of chromosome 14 in a large kindred with Alzheimer's disease (L. R. Weitkamp, Am. J. Hum. Genet. 35:443–53 (1983)), and by the altered immunological parameters in Down's syndrome, a disease whose symptoms are similar to senile dementia of the Alzheimer's type (SDAT).

Scientists in the nascent field of neuroinimunology have hypothesized that the defects in the function of brain cells (neurons) may be observed concomitantly as parallel defects or deficiencies in receptors on the cells of the immune system (such as peripheral blood immune cells). The validity of this hypothesis was recently brought to light with the aforementioned discovery of HIV infection in neurons. This neuroimmunologic theory has had significant impact because formerly almost all neuropsychiatric disorders were thought to be primarily due to factors such as genetic predisposition, mental attitudes, and/or resistance to natural environment rather than defects or deficiencies in cell function. Similarly, though the immune system has been implicated in numerous diseases ranging from infection to cancer to degenerative diseases such as Alzheimer's disease, arthritis, and aging, its relationship to cognitive function was previously unrealized.

Because the chemical interrelationship between these diverse physiological systems has been recognized only recently, prior art and medical treatments and pharmaceutical agents have focused almost exclusively on treating the individual systems alone. Thus, pharmaceutical compounds have been developed for treating or regulating the cardiovascular system or the immune system or the central nervous system with the idea of avoiding undesirable interactions in what are now known to be related physiological systems. By far the greatest amount of recent effort in the pharmaceutical and medical fields has been devoted to the treatment or regulation of the immune system alone. Numerous immunomodulating and antiviral agents have been disclosed in the art such as those described in European Patent Application Publication No. 0126813 by Simon et al., U.S. Pat. No. 4,221,909 to Simon et al., U.S. Pat. No. 4,211,794 to Kraska, and U.S. Pat. No. 4,221,910 to Giner-Sorolla. Unlike antibiotics which directly attack or destroy invading organisms such as bacteria, immunomodulating agents and more specifically immune enhancing agents are compounds which help to bolster the body's own defense mechanisms against the effects of infections. Immunomodulators either restore depressed immune function, or suppress hyperactive immune function.

Accordingly, there is a need for compounds that are bifunctional and that can interact with multiple receptors on the surface of different cell types. There is also a particular need for compounds that bypass the blood-brain barrierso that the activities of such compounds can be exerted in the central nervous system, such as for the treatment of diseases such as Alzheimer's disease, amyotrophic lateral sclerosis (Lou Gehrig's disease), and other neurodegenerative diseases.

A number of such compounds and methods for synthesizing them are disclosed in U.S. Pat. No. 5,091,432 to Glasky, incorporated herein by this reference. This includes a number of bifunctional compounds that bypass the blood-brain barrier, particularly 4-carboxyphenyl-3-(6-oxohydropurin-9-yl) propanamide. Other synthetic methods for analogous compounds are those described in G. Shaw et al., "Purines, Pyrimidines, and Glyoxalines. Part XIII. Some New Unambiguous Syntheses of 5-Aminoglyoxalines and 5-Aminoglyoxaline-4-carboxamides, and a Synthesis of 5-Amino-1-p-D-ribofuranosylglyoxaline-4-carboxyamide," J. Chem. Soc. 1959: 1648 (1959), incorporated herein by this reference, and in P. R. Birkett et al., "Synthesis and Intramolecular Cyclisation of 5-Aminoimidazolealkanoates and Their Conversion to Purine Derivatives, "Synthesis 1991 157-159 (1991), also incorporated herein by this, reference, which describes the synthesis of ethyl (9-hypoxanthinyl)alkanoates. The biosynthetic pathways for purines are also known and are described, for example, G. M. Blackburn & M. J. Gait, Nucleic Acids in Chemistry and Biology (2d ed., Oxford University Press, 1996), pp. 148152, also incorporated herein by this reference.

Although synthetic methods for these bifunctional compounds, particularly N-4-carboxyphenyl-3-(6-oxohydropurin-9-yl) propanamide, are known, there is a need for an improved synthetic method for these compounds. There is a particular need for a more efficient synthesis that provides higher yields and fewer side-reactions as well as providing a pure product.

SUMMARY

An improved method of synthesizing such bifunctional compounds comprises:
  (1) reacting aminocyanacetamide with triethyl orthoformate to form an imidoester derivative of aminocyanacetamide;
  (2) forming a compound having a reactive amino group on a hydrocarbyl moiety, t5 the hydrocarbyl moiety being linked through an amide group to a physiologically active moiety or an esterified derivative of a physiologically active moiety including therein an esterified benzoyl group;
  (3) reacting the imidoester with the compound having the reactive amino group on the hydrocarbyl moiety to form a derivative of 5-aminoimidazole-4-carboxamide substituted at the 1-position with a hydrocarbyl moiety linked through an amide group to a physiologically active moiety including therein an optionally esterified benzoyl group;
  (4) forming the six-membered heterocyclic ring of the purine moiety of the hypoxanthine by reacting the derivative of 5-aminoimidazole-4-carboxamide formed in step (3) with triethyl orthoformate to form a 9-substituted hypoxanthine compound substituted at the 925 position with a hydrocarbyl moiety linked through an amide group to a physiologically active moiety including therein an optionally esterified benzoyl group; and
  (5) hydrolyzing the ester of the optionally esterified benzoyl group if present.

Typically, the hydrocarbyl moiety has the structure $(CH_2)_n$, wherein n is an integer from 1 to 6; preferably, n is 2.

In one preferred embodiment, the physiologically active moiety is p-aminobenzoic acid. In this embodiment, the esterified benzoyl is typically esterified with a linear or branched alkyl group of from 1 to 7 carbon atoms. Preferably, the esterified benzoyl is esterified with a group with the structure $CH_3—(CH_2)_z$, where z is an integer from 0 to 6. More preferably, z is 1.

The compound having the reactive amino group linked to the hydrocarbyl moiety can be formed by a process comprising the steps of:
  (1) activating an ω-aminocarboxylic acid with thionyl chloride; and
  (2) reacting the activated o)-aminocarboxylic acid with a p-aminobenzoic acid ester in the presence of a tertiary amine selected from the group consisting of triethylamine and ethyldiisopropylamine, wherein the p-aminobenzoic acid ester is esterified with a linear or branched alkyl group of from 1 to 7 carbons.

Typically, the alkyl group is ethyl. In one preferred embodiment, the ω-aminocarboxylic acid is 3-aminopropionic acid. Preferably, the tertiary amine is triethylamine.

One particularly preferred embodiment of the present invention is a process of synthesizing the 9-substituted hypoxanthine derivative N-4-carboxyphenyl-3-(6-oxohydropurin9-yl) propanamide. This process comprises the steps of:
  (1) forming ethyl 4-(P-alanyl) aminobenzoate by a process including the steps of:
    (a) activating 3-aminopropionic acid with thionyl chloride; and
    (b) reacting the activated 3-aminopropionic acid with ethyl paminobenzoic acid in the presence of triethylamine in a solvent comprising toluene and dichloromethane;
  (2) reacting aminocyanacetamide with triethyl orthoformate in acetonitrile to form an imidoester derivative of aminocyanacetamide;
  (3) reacting the imidoester with ethyl 4-(D-alanyl) aminobenzoate in acetonitrile/methanol;
  (4) forming the six-membered ring of the purine moiety of the hypoxanthine by reacting the ester formed in step (3) with triethyl orthoformate in acetic acid; and (5)

hydrolyzing the ester group of the compound formed in step (4) to yield N-4-carboxyphenyl-3-(6-oxo-hydropurin-9-yl) propanamide.

BRIEF DESCRIPTION OF THE DRAWINGS

These and other features, aspects, and advantages of the present invention will become better understood with reference to the following description, appended claims, and accompanying drawings where:

DESCRIPTION

Figure 1:
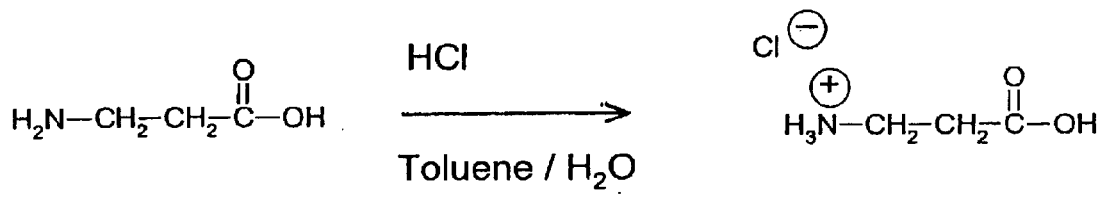
FIG. 1 is a reaction scheme (Scheme 1) for conversion of an c)-aminocarboxylic acid such as β-alanine to its hydrochloride.

An improved method of synthesis of the compound N-4-carboxyphenyl-3-(6-oxohydropurin-9-yl) propanamide involves:

(1) reaction of aminocyanacetamide with triethyl orthoformate to form an imidoester derivative of aminocyanacetamide;

(2) formation of a compound having a reactive amino group on a hydrocarbyl moiety, the hydrocarbyl moiety being linked through an amide group to a physiologically active moiety or an esterified derivative of a physiologically active moiety including therein an esterified benzoyl group;

(3) reaction of the imidoester with the compound having the reactive amino group on the hydrocarbyl moiety to form a derivative of 5-aminoimidazole-4-carboxamide substituted at the 1-position with a hydrocarbyl moiety linked through an amide group to a physiologically active moiety including therein an optionally esterified benzoyl group;

(4) formation of the six-membered heterocyclic ring of the purine moiety of the hypoxanthine by reacting the derivative of 5-aminoimidazole-4-carboxamide formed in step (3) with triethyl orthoformate to form a 9-substituted hypoxanthine compound substituted at the 9position with a hydrocarbyl moiety linked through an amide group to a physiologically active moiety including therein an optionally esterified benzoyl group; and (5) hydrolysis of the ester group if present.

Each of these steps will be discussed below in detail, with particular reference to the synthesis of N-4-carboxyphenyl-3-(6-oxohydropurin-9-yl) propanamide. However, other bifunctional compounds that are 9-substituted hypoxanthine derivatives can be prepared by analogous methods. These other hypoxanthine derivatives can use linkers of different lengths between the hypoxanthine moiety and the physiologically active moiety that contains an aromatic ring such as a benzoyl group; the aromatic ring can also be substituted. Some of these alternatives are discussed below with respect to intermediates used in particular steps of the synthesis.

There are several alternative routes for this synthesis. In the first route, the benzoyl group of the physiologically active moiety remains esterified until the last step of the synthesis. At that stage, the ester group is removed by hydrolysis to produce the final product. In a second route, the ester group is removed earlier by hydrolysis to yield a free benzoic acid moiety. Typically, in this second route, the amino group of the compound having a reactive amino group on a hydrocarbyl moiety linked through an amide group to a physiologically active moiety is protected by a protecting group such as benzyloxycarbonyl (Z). Alternatively, other protecting groups of the types generally used to protect amino termini in peptide chemistry can be used, such as t-butyloxycarbonyl (Boc), the biphenylyl analogue of Boc (Bpoc), or 9fluorenylmethyloxycarbonyl (Fmoc). Other suitable protecting groups are also known in the art. The general principle for choosing the protecting group is to protect the amino group during activation of the carboxyl group with ethyl chloroformate and formation of the carboxamide with ethyl 4-aminobenzoate and to eliminate the protecting group afterwards without cleaving the alanine-aminobenzoic acid bond. The routes are interconnected by the hydrolysis of the ester group at several points, as shown below.

I. First Route in Which Benzoyl Group Remains Esterified

Formation of Compounds Having a Reactive Amino Group on a Hydrocarbyl Moiety Linked to Esterified Benzoyl Group The first step of the reaction is formation of a compound having a reactive amino group on a hydrocarbyl moiety. The hydrocarbyl moiety is linked through an amide group to a physiologically active moiety or an esterified derivative of a physiologically active moiety including therein an esterified benzoyl group. This portion of the synthesis contributes the linker portion and the physiologically active compound.

The hydrocarbyl moiety has the structure $(CH_2)_n$, wherein n is an integer from 1 to 6. In one particularly preferred embodiment of a process according to the present invention, n is 2. The length of the hydrocarbyl moiety determines the distance between the hypoxanthine moiety and the physiologically active moiety.

In one particularly preferred embodiment of a process according to the present invention, the physiologically active moiety is p-aminobenzoic acid. Typically, the benzoyl moiety is esterified with a linear or branched alkyl group of from 1 to 7 carbon atoms. In this embodiment, the benzoyl moiety is preferably esterified with a group with the structure $CH_3(CH_2)$, where z is an integer from 0 to 6. Most preferably, z is 1.

The first step in this process is the conversion of an (o-aminocarboxylic acid such as β-alanine to its hydrochloride. This is shown in Scheme 1 below (FIG. 1) with respect to β-alanine being converted into β-alanine hydrochloride, but, as detailed below, the steps can be performed with other ω-carboxylic acids. Step 1 is preferably performed in toluene with a small proportion of water. The hydrochloric acid is typically present in molar excess (i.e. typically at least about 150% with respect to the amount of β-alanine). Water is preferably present at about 0.5% (v/v). The reaction preferably runs in a slurry. The β-alanine is preferably milled or micronized. The reaction can be run at room temperature or at an elevated temperature of 30–35° C. The reaction is preferably run for at least about 8 hours; it can be run for as long as 24 hours. Although the reaction has been described with P-alanine, it can be performed with other (oaminocarboxylic acids. The (ω-aminocarboxylic acid ω-alanine is 3-aminopropionic acid. Changing the ω-aminocarboxylic acid used changes the length of the linker in the final: product. For example, if 4-aminobutanoic acid is used instead of 3-aminopropionic acid, the length of the linker increases by 1 carbon atom.

Figure 2:
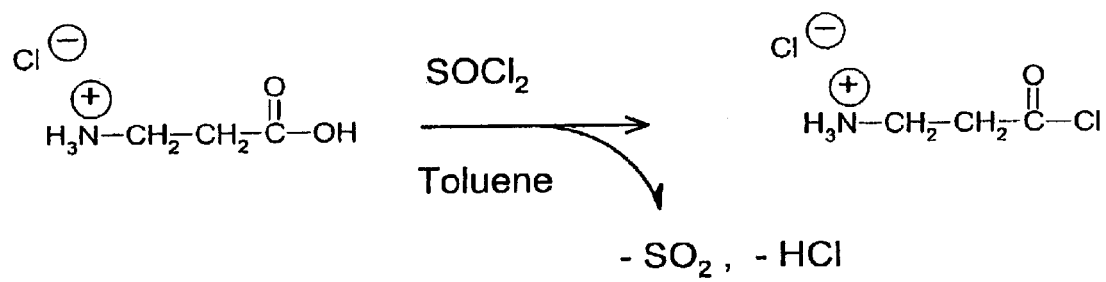
FIG. 2 is a reaction scheme (Scheme 2) for conversion of the hydrochloride of ω-aminocarboxylic acid such as P-alanine to its acyl chloride hydrochloride.

The second step is the conversion of the hydrochloride of (o-aminocarboxylic acid such as β-alanine to its acyl chloride hydrochloride. This is shown in Scheme 2 (FIG. 2), below. This step is preferably performed in toluene. Preferably, a molar excess of thionyl chloride is used of at least 200%. Preferably, the thionyl chloride is present at about 600% molar ratio. The reaction is typically performed at a temperature of about 40–50° C., preferably at about 45–50° C., most preferably at about 50° C. The reaction time used for this step varies to some extent with the temperature, but is at least 8 hours and can be as long as 39 hours. A preferred set of reaction conditions is 50° C. for 38 hours. Unreacted thionyl chloride and toluene are then removed by distillation at reduced pressure, such as at 50° C., 100 mbar.

The next step is the reaction of the acyl chloride hydrochloride formed in Scheme 2 with a lower alkyl ester of an aminobenzoic acid. Preferably, the aminobenzoic acid is paminobenzoic acid. The lower alkyl ester is typically an ethyl ester. As used herein, the term "lower alkyl" refers to a branched or unbranched alkyl group of from 1 to 7 carbon atoms. Preferably, the alkyl group has the structure $CH_3-(CH_2)_z$, where z is an integer from 0 to 6. A particularly preferred lower alkyl group for the ester is ethyl and therefore a particularly preferred ester is ethyl p-aminobenzoate. This is related to the physiologically active compound p-aminobenzoic acid. However, other benzoic acid derivatives can be used at this stage. For example, the aromatic ring can have other substituents.

Figure 3:
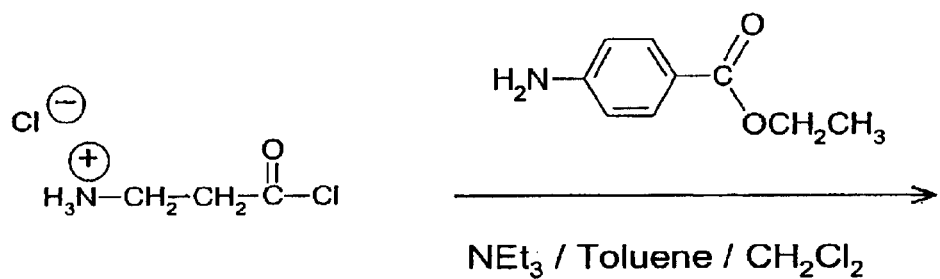
FIG. 3 is a reaction scheme (Scheme 3) for reaction of the acyl chloride hydrochloride formed in Scheme 2 (FIG. 2) with a lower alkyl ester of an aminobenzoic acid.
Figure 3:
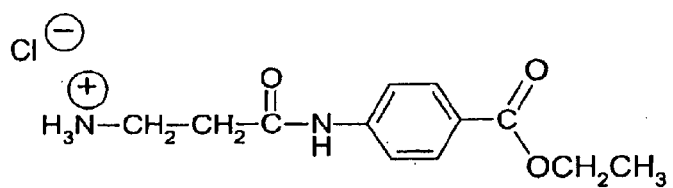

With ethyl p-aminobenzoate, the reaction occurs as is shown below in Scheme 3 (FIG. 3).

Typically, the reaction is performed in the presence of triethylamine at a molar ratio of about 1:1 with the ester. The reaction is preferably performed in dichloromethane. In one preferred mode of performing the reaction, a solution containing the ester and triethylamine in dichloromethane is slowly added to a suspension of the acyl chloride in toluene from step 2. Typically, addition of the ester and triethylamine to the acyl chloride occurs slowly at a temperature of about 45–55° C. The reaction is then allowed to proceed for about 16–20 hours at a temperature of about 40° C. In general, it is preferred to add the ester in a solution in which triethylamine is already present.

Other possible variables for the reaction conditions are described below.

Preferably, the product is isolated by filtration at 40° C., washed three times with dichloromethane and dried under vacuum at 40° C. overnight. However, other purification procedures, such as extraction, can be used. In general, the use of the direct filtration step is preferred.

Figure 4:
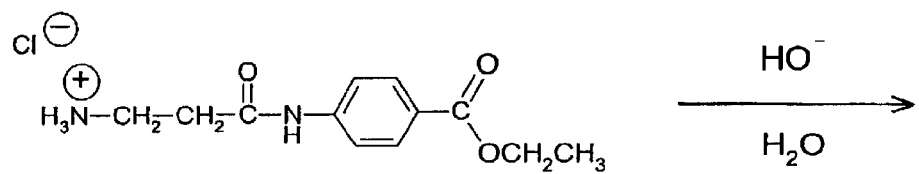
FIG. 4 is a reaction scheme (Scheme 4) for neutralization of the quaternary ammonium with a base to yield an ester containing a reactive amino group.
Figure 4:
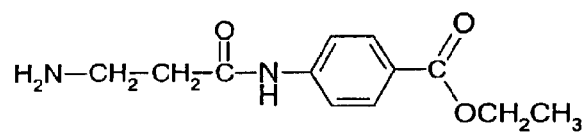

The next step is the neutralization of the quaternary ammonium formed by the preceding steps with a base to yield the ester with an uncharged amino group. This is shown in Scheme 4 (FIG. 4). Preferably, this reaction is performed in water:ethanol (9:1; w/w). The neutralization reaction is typically performed at pH 10.0 by addition of an aqueous base. The aqueous base is typically used in a molar excess, preferably about 1.6 moles per mole of ester hydrochloride. Preferably, the base used is sodium hydroxide, but another alkali metal hydroxide such as potassium hydroxide or lithium hydroxide or an alkaline earth hydroxide such as calcium hydroxide or barium hydroxide can be used. As another alternative, an organic alkoxide such as sodium ethoxide, potassium ethoxide, sodium methoxide, or potassium methoxide can be used. However, it is generally preferred to use sodium hydroxide.

When sodium hydroxide is used, the crystallization process startsspontaneously at pH 9.7 and a thick and hardly stirrable slurry is obtained. The slurry is diluted with a mixture of water/ethanol (90:10, w/w) and the suspension is stirred. The ethyl ester is isolated by filtration, washed with water:ethanol, and dried under vacuum. As an alternative, the neutralization can be performed by crystallization of the free amino form from an alkaline aqueous solution after the solution of the ester hydrochloride in water (pH 2.0) and adjustment of pH with a base as discussed above, preferably sodium hydroxide, to a pH of 12.3. In this alternative, the final product contains some 4-aminobenzoic acid ethyl ester (i.e., cleavage of the amide link) but the formation of this impurity can be reduced by using an ethanol/water mixture (5% w/w) in the neutralization step.

As an alternative to the synthesis of the ester containing the reactive amino group, beginning with P-alanine or an analogous compound, the ester containing the reactive amino group can be supplied in protected form, such as protected with a benzyloxycarbonyl (Z) group, deprotected, and then added in methanol solution. Alternatively, other protecting groups can be used.

Figure 5:
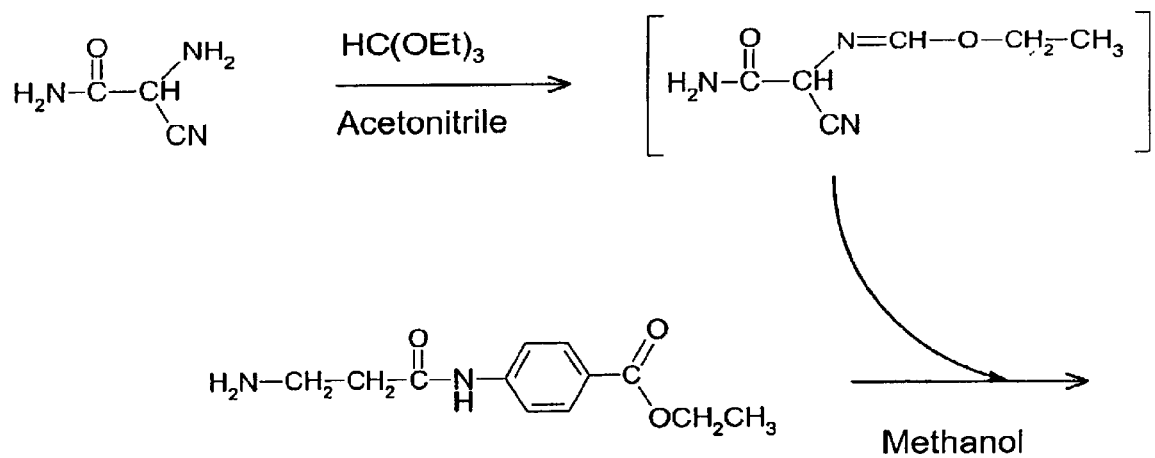
FIG. 5 is a reaction scheme (Scheme 5) for the formation of an imidoester from aminocyanacetamide and the reaction of the imidoester with the ester containing the reactive amino group from Scheme 4.
Figure 5:
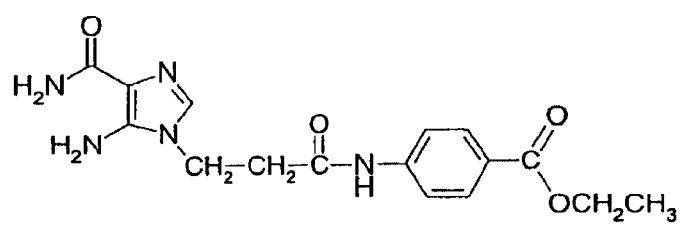

The next step is the formation of an imidoester from aminocyanacetamide and the reaction of the imidoester with the ester containing the reactive amino group. Aminocyanacetamide is commercially available or can be synthesized by a number of routes. One route for the synthesis of aminocyanacetamide is described in EPO Patent Publication No. 0924195, by Muiller et al. (EPROVA Aktiengesellschaft), published Dec. 7, 1998, and incorporated herein in its entirety by this reference. The imidoester is typically formed in situ and is not separately isolated. Typically, the imidoester formation occurs in acetonitrile and a slight molar excess of triethyl orthoformate is used. This step is referred to as a cyclocondensation. A preferable molar ratio of triethyl orthoformate to aminocyanacetamide is about 1.08. The concentration of aminocyanacetamide in the acetonitrile is preferably about 1 gram of aminocyanacetamide per 13 ml of acetonitrile, although the reaction can be performed at higher or lower concentrations of aminocyanacetamide in acetonitrile. The reaction can be performed at a temperature from about 35° C. to about 65° C. preferably at about 40° C. to about 54° C. However, it is generally preferred to begin the reaction at a temperature in the higher portion of this range, from about 50° C. to about 54° C. The reaction of the imidoester with the ester containing the reactive amino group can be performed in tetrahydrofuran under reflux or in other solvents such as methanol, ethanol, or ethyl acetate. However, to avoid the necessity of isolation of the unstable imidoester, it is generally preferred to perform this step in acetonitrile, as the imidoester can be formed and is relatively stable in this solvent. The result of this step is the formation of the derivative of 5-aminoimidazole-4-carboxamide ("AICA") substituted at the 1-position with the hydrocarbyl moiety linked through the amide group to the physiologically active moiety including therein the esterified benzoyl group. It is also preferred to dose the compound having the reactive amino group to the imidoester. This reaction is outlined below in Scheme 5 (FIG. 5). It is strongly preferred to perform the reaction at at least 35° C. to prevent the formation of undesired contaminants and side reactions.

Preferably, the ester containing the reactive amino group is used at about 0.9 equivalents per mole of aminocyanacetamide.

After the cyclocondensation, the product is typically isolated by suction filtration or centrifugation. It is preferred to wash the product thoroughly with methanol until the effluent is colorless.

Preferably, the product is then dried at 45–50° C. in vacuo. It is preferred to use a drying temperature of no higher than about 50° C. to prevent the generation of HCN.

Figure 6:
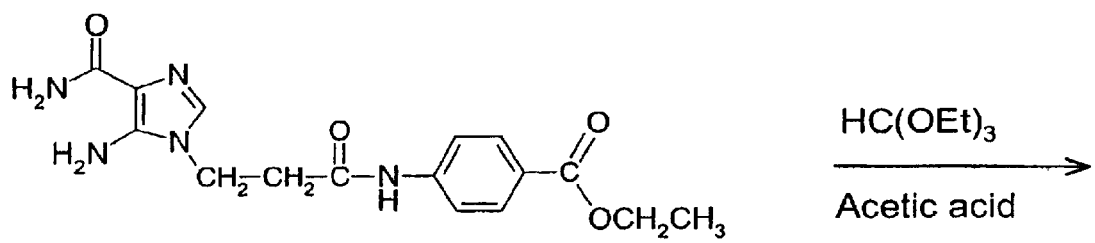
FIG. 6 is a reaction scheme (Scheme 6) for cyclization of the ester or 1-substituted 5-aminoimidazole-4-carboxamide with triethyl orthoformate to produce the six-membered ring of a purine moiety.
Figure 6:
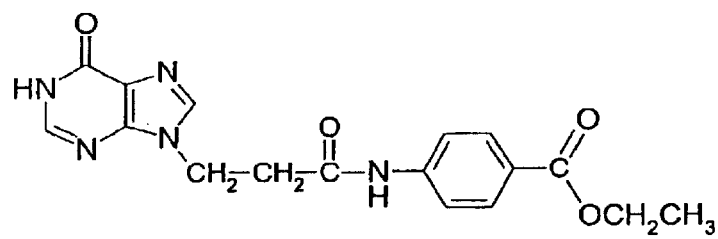

The next step in the reaction is the cyclization of the derivative of 5-aminoimidazole-4-carboxamide with triethyl orthoformate to produce the six-membered ring of the purine moiety. The cyclization reaction is performed in an organic acid. This reaction is shown in Scheme 6 (FIG. 6). Typically, the organic acid is formic acid or acetic acid. Preferably, the organic acid is acetic acid. In acetic acid, the cyclization reaction is preferably performed at boiling temperature. In acetic acid, triethyl orthoformate is preferably present at about 3 moles per mole of derivative of 5-aminoimidazole-4-carboxamide. In acetic acid, the reaction goes substantially to completion after about 2 hours and goes to completion at about 4.5 hours. A preferred temperature is about 97–106° C. The ratio of acetic acid solvent to derivative of 5-aminoimidazole-4-carboxamide typically varies from about 3 ml acetic acid per gram of derivative to about 7.2 ml of acetic acid per gram of derivative. In acetic acid, the desired product is virtually insoluble and the contaminants are soluble.

Alternatively, the reaction can be performed in a mixture of acetic acid and formic acid.

Preferably, the reaction product is isolated by suction filtration or centrifugation and washed thoroughly with acetic acid and then with ethanol.

Figure 7:
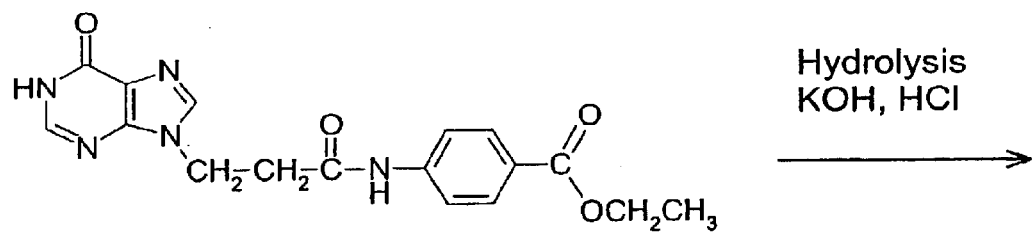
FIG. 7 is a reaction scheme (Scheme 7) for hydrolysis of the ester moiety bound to the benzoyl group to produce the final product, a 9-substituted hypoxanthine derivative.
Figure 7:
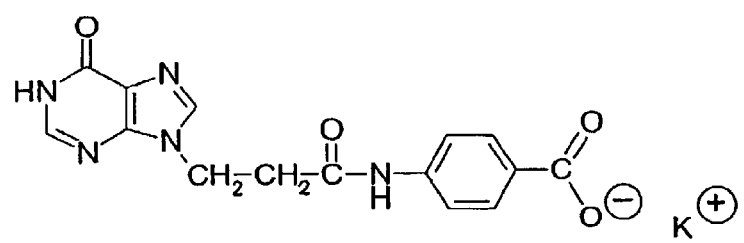

The final step in this route is the hydrolysis of the ester moiety bound to the tf) benzoyl group. This is shown in Scheme 7 (FIG. 7). Hydrolysis is preferably performed in an aqueous solution. It is preferred to use a hydroxide of an alkali metal such potassium hydroxide or sodium hydroxide; potassium hydroxide is particularly preferred. Typically, a slight molar excess of base is used. This can range from about 1.037 to about 1.153 equivalents of base. The reaction can be performed overnight at room temperature. The product to be hydrolyzed dissolves exothermically, so that the temperature of the reaction begins at about 31° C.

After hydrolysis is complete or substantially complete, the preparation is neutralized with an aqueous strong acid. A particularly preferred strong acid is HCl. A preferred concentration of HCl is between about 1.0 N and 37% aqueous HCl. The optimal amount of HCl is approximately an equivalent amount based on the amount of KOH when the base is KOH and the acid is HCl.

Alternatively, the hydrolysis can be performed with an alkali metal hydroxide without subsequent neutralization with an acid.

The crude product can be treated inan alkaline aqueous ethanolic soluiion to obtain a crystal structure with maximum solubility.

It is strongly preferred to monitor the course of hydrolysis by HPLC. During the course of hydrolysis, hydrolysis of the amide group is to be avoided.

Preferably, the hydrolysis is performed at a temperature of at least about 25° C. but not higher than about 50° C. Preferably, hydrolysis is carried out by adding the ester to be hydrolyzed to the aqueous solution of the alkali metal hydroxide over a period of from about 15 minutes but not longer than about 30 minutes.

II. Second Route with Free Benzoic Acid Group

As an alternative, the 9-substituted hypoxanthine derivative can be synthesized by an alternative route in which the ester moiety of the benzoyl ester is hydrolyzed prior to reaction with the imidoester. Typically, in this route, the amino group of the compound that includes the ED reactive amino group on the hydrocarbyl moiety is initially blocked or protected with a protecting group such as benzyloxycarbonyl (Z) or other protecting groups of the types generally used to protect amino termini in peptide chemistry, such as t-butyloxycarbonyl (Boc), the biphenylyl analogue of Boc (Bpoc), or 9-fluorenylmethyloxycarbonyl (Fmoc). Other suitable protecting groups are also known in the art.

Figure 8:
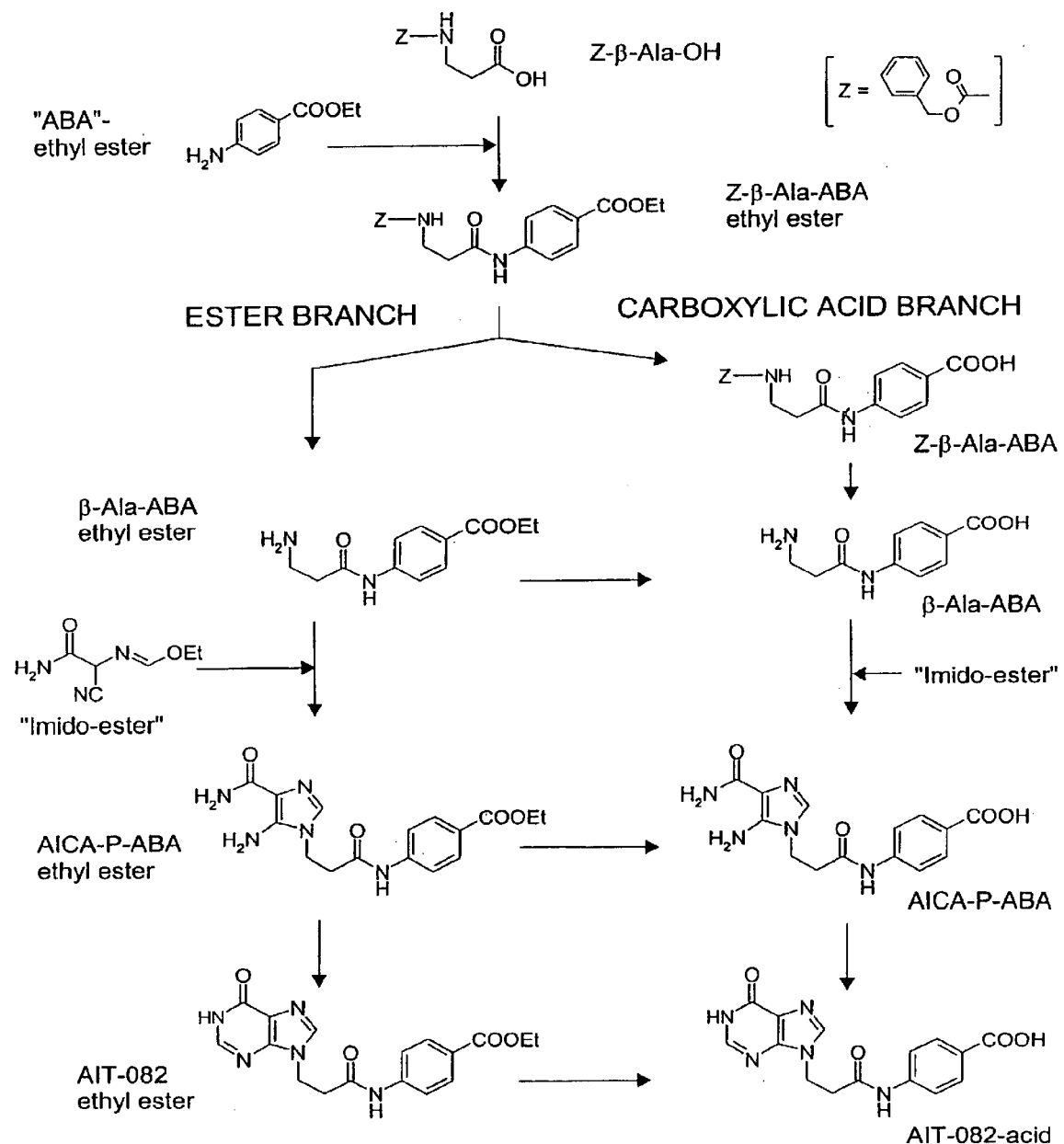
FIG. 8 is a reaction scheme (Scheme 8) showing the relationship between the two branches of the pathway, one utilizing intermediates in which the benzoyl group linked to the hydrocarbyl moiety is esterified, and the other utilizing intermediates in which the benzoyl group linked to the hydrocarbyl moiety is not esterified, as well as routes of interconversion between the branches.

In general, this route is shown in Scheme 8 (FIG. 8).

First, the benzyloxycarbonyl derivative of P-alanine is reacted with the ethyl ester of p-aminobenzoic acid to form benzyloxycarbonyl-p-alanyl aminobenzoic acid ethyl ester. Typically, this reaction is performed in dichloromethane in the presence of triethylamine and ethyl chloroformate. A preferred molar ratio of the benzyloxycarbonyl derivative of β-alanine to the ethyl ester of p-aminobenzoic acid is about 1:1.

The second step is the hydrolysis of the ester group of benzyloxycarbonyl-β-alanyl aminobenzoic acid ethyl ester to produce benzyloxycarbonyl-p-alanyl aminobenzoic acid. One method of performing this hydrolysis step is basic hydrolysis, such as in sodium hydroxide at 40°–60° C. for about 10 hours in a solution or a slurry. The resulting hydrolyzed product is then acidified under relatively mild conditions, such as at about pH 3.5 to about 4.0, preferably about pH 3.6, to precipitate the product. This hydrolysis is the entry point for the carboxylic acid branch of the pathway.

The third step is the deblocking or removal of the benzyloxycarbonyl group by hydrogenolysis. This is preferably performed in tetrahydrofuran in the presence of a palladium catalyst slurried in methanol or ethanol; preferably the palladium catalyst is slurried in methanol. The catalytic hydrogenolysis can be performed at room temperature.

The fourth step is the condensation of the deblocked intermediate with the imidoester to form a 1-substituted-5-aminoimidazole-4-carboxamide as described above. This can be performed under conditions substantially similar to those described above for the corresponding reaction forming the 1-substituted aminoimidazole-4-carboxamide in Route I, above.

The fifth and final step in this route is the condensation of the 1-substituted-5-aminoimidazole-4-carboxamide with triethyl orthoformate to produce the six-membered ring of the purine moiety. This step is performed substantially as in Route I, above. This step directly produces the 9-substituted hypoxanthine derivative, as no final hydrolysis step is required.

The first and second routes are interconnected by the possible hydrolysis of the ester group of intermediates of the first route to convert the intermediates into intermediates that are in the second route. For example, the 13-alanyl-p-aminobenzoic acid ethyl ester that is the intermediate that reacts with the imidoester in the first route can be hydrolyzed to β-alanyl p-aminobenzoic acid by treatment with 0.1 N NaOH in methanol such as at 40° C. for 30 minutes. The resulting β-alanyl p-aminobenzoic acid can then be reacted with the imidoester in the second route. Similarly, the 1-substituted 5-aminoimidazole-4-carboxamide intermediate containing the esterified benzoyl moiety of the first route that can undergo condensation with triethyl: orthoformate to complete the six-membered purine ring can be hydrolyzed to the 1-substituted 5-aminoimidazole-4-carboxamide intermediate of the second route. This hydrolysis can be performed by a basic hydrolysis step, such as in 0.5 N NaOH at a temperature of 70–80° C. for 10 hours. Other basic hydrolysis conditions can alternatively be used. The resulting intermediates can undergo the remaining reactions of the second branch as described above.

The invention is illustrated by the following Examples. These Examples are presented for illustration only and are not intended to limit the invention. The Examples are presented in terms of the final synthesis of N-4-carboxyphenyl-3-(6-oxohydropurin-9-yl) propanamide.

EXAMPLE 1

Synthesis of β-Alanine Hydrochloride

Micronized fine powder of P-alanine (1.000 kg, 11.22 mol) was suspended in toluene (9.78 kg) containing water (0.056 kg). The white suspension was treated with HCl gas under vigorous stirring at room temperature (slightly exothermic reaction). After 8 h the salification reaction with the HCl gas (total amount used 654 g) was almost complete (97.4% chloride).

EXAMPLE 2

Conversion of β-Alanine Hydrochloride to its Acyl Chloride Hydrochloride

Thionyl chloride (8.026 kg, 67.41 mol) was slowly added to the thick white suspension of Example 1 under vigorous stirring (strong gas formation). After 1 h the reaction mixture was heated up to a jacket temperature of 50° C. (gentle gas formation) for 38 h.

Unreacted thionyl chloride and toluene (weight reduction 8.905 kg) were distilled off under vacuum (50° C., 100 mbar) to yield the acyl chloride hydrochloride.

EXAMPLE 3

Condensation of Acyl Chloride Hydrochloride with p-Aminobenzoic Acid Ethyl Ester A solution containing p-aminobenzoic acid ethyl ester (1.850 kg, 11.22 mol) and triethylamine (1.14 kg, 11.22 mol) in dichloromethane (11.87 kg) was slowly added (47 min) to the slightly yellow suspension of the acyl chloride hydrochloride from Example 2 at a temperature of 45–55° C. and the reaction mixture was stirred overnight (17 h) at a jacket temperature of 400° C. (reaction control by HPLC). The product was isolated by filtration (400° C.), washed 3 times with dichloromethane (3×2.64 kg) and dried under vacuum at 40° C. overnight. The yield was 3.937 kg of P-alanyl-p-aminobenzoic acid ethyl ester hydrochloride (80.37% of theoretical corrected) HPLC yielded 62.5% w/w, 98.22% area. Some triethylamine hydrochloride precipitates together with the product and causes a crude weight of greater than 100% of theoretical. The triethylamine hydrochloride does not interfere and is eliminated in the next step (Example 4).

EXAMPLE 4

Conversion of Ester Hydrochloride to Ester by Neutralization

The ester hydrochloride from Example 3 (2.000 kg, 4.58 mol) was dissolved in water (18.0 kg) and ethanol (2.0 kg). The acidic pH of the solution (pH 0.54) was adjusted to pH 10.0 by addition of sodium hydroxide (30% NaOH, 1059.2 g, 7.94 mol). The crystallization process starts spontaneously at pH 9.7 and a thick and hardly stirrable slurry was obtained. After dilution (500 g) with a mixture of water/ethanol (9: 1, w/w) the thick suspension was stirred for 2 h at room temperature. The β-alanyl-p-aminobenzoic acid ethyl ester was isolated by filtration, washed twice (2×1.0 kg) with water/ethanol (9:1 w/w) and dried under vacuum at 40° C. overnight. The yield was 1.100 kg of ethyl ester, 106.9% of theoretical corrected. HPLC yielded 105.20% (w/w), 99.34% area. The assay corrected yield was greater than 100% of theory probably due to non-homogeneous hydrochloride.

EXAMPLE 5

Cyclocondensation of Imidoester and β-Alanyl-p-Aminobenzoic Acid Ethyl Ester

To the solution of imidoester, formed in situ by the reaction of aminocyanacetamide (30 g; 0.30 mol) in acetonitrile (500 ml) and triethyl orthoformate (55 ml; 0.33 mol) at boiling temperature, there was added at 30° C. a solution of β-alanyl p-aminobenzoic acid ethyl ester (71 g; 0.30 mol) in methanol (300 ml) and the soon precipitating AICA-p-ABA ethyl ester ("AIP-ester") was isolated after 2 h. The yield was 77.5 g.

EXAMPLE 6

Cyclization and Formation of Purine Ring with Triethyl Orthoformate

The product from the cyclocondensation of the imidoester and P-alanyl paminobenzoic acid ethyl ester ("AIP-ester") was cyclized with triethyl orthoformate in acetic acid. The AIP-ester (200 g; 0.58 mol) was dissolved in glacial acetic acid (1440 ml) after the addition of triethyl orthoformate (258 g; 1.74 mol), the yellow solution was kept at boiling temperature for 4.5 h. The reaction product was isolated by filtration. The yield was 2118 g.

EXAMPLE 7

Hydrolysis of Ester Group to Produce N-4-Carboxyphenyl-3-(6-Oxohydropurin-9-yl) Propanamide The cyclized ester from Example 6 (3.5 g) was slurried in aqueous KOH (40 ml water, 1.96 g; 0.03 mol KOH 85%). The solid dissolved exothermically (up to 31° C.). The solution was left overnight at room temperature and afterwards neutralized until the pH reached 6.7 (21 ml 1.0 N HCl; 0.02 mol). Below pH 7.9 a very fine precipitate started to be formed which was isolated, washed with water and ethanol and dried at 40° C. under vacuum. The yield was 2.40 g.

ADVANTAGES OF THE INVENTION

The synthetic methods of the present invention provide an efficient and economical method of synthesizing 9-substituted hypoxanthine derivatives, particularly N-420 carboxypheny 1-3-(6-oxohydropurin-9-yl) propananide.

This method uses available starting materials, requires a minimum number of steps, and provides a product of high purity with a minimum of purification. The procedure avoids side reactions that complicate isolation and purification of the final product.

Although the present invention has been described in considerable detail, with reference to certain preferred versions thereof, other versions and embodiments are possible. Therefore, the scope of the invention is determined by the following claims.

We claim:

1. A process of synthesizing the 9-substituted hypoxanthine derivative N-4-carboxyphenyl-3-(6-oxopurin-9-yl) propanamide comprising the steps of:
   (a) forming ethyl 4-(B-alanyl) aminobenzoate by a process including the steps of:
      (i) activating 3-aminopropionic acid with thionyl chloride; and
      (ii) reacting the activated 3-aminopropionic acid with ethyl paminobenzoate in the presence of triethylamine in a solvent comprising toluene and chloroform;
   (b) reacting aminocyanacetamide with triethyl orthoformate in the presence of acetonitrile to form an imidoester derivative of aminocyanacetamide;
   (c) reacting the imidoester derivative with ethyl 4-($\beta$-alanyl) aminobenzoate in methanol;
   (d) forming the six-membered ring of the purine moiety of the hypoxanthine by reacting the ester formed in step (c) with triethyl orthoformate in acetic acid; and
   (e) hydrolyzing the ester group of the compound formed in step (d) to yield N-4-carboxyphenyl-3-(6-oxopurin-9-yl) propanamide.

* * * * *

UNITED STATES PATENT AND TRADEMARK OFFICE
CERTIFICATE OF CORRECTION

PATENT NO. : 6,849,735 B1
DATED : February 1, 2005
INVENTOR(S) : Alvin J. Glasky, Heinrich Bollinger and Hans Rudolf Muller It is certified that error appears in the above-identified patent and that said Letters Patent is hereby corrected as shown below:

<u>Column 14,</u>
Line 2, should read -- p-aminobenzoate -- and not "paminobenzoate"

Signed and Sealed this

Third Day of May, 2005

JON W. DUDAS
*Director of the United States Patent and Trademark Office*